United States Patent [19]

Moser

[11] Patent Number: 4,534,904

[45] Date of Patent: * Aug. 13, 1985

[54] PROCESS FOR PRODUCING N-PHOSPHONOMETHYLGLYCINE

[75] Inventor: Hans Moser, Magden, Switzerland

[73] Assignee: Ciba-Geigy Corporation, Ardsley, N.Y.

[*] Notice: The portion of the term of this patent subsequent to Jan. 18, 2000 has been disclaimed.

[21] Appl. No.: 630,626

[22] Filed: Jul. 13, 1984

Related U.S. Application Data

[60] Division of Ser. No. 442,933, Nov. 19, 1982, Pat. No. 4,486,358, which is a continuation-in-part of Ser. No. 391,816, Jun. 24, 1982, abandoned, which is a continuation-in-part of Ser. No. 327,138, Dec. 3, 1981, Pat. No. 4,369,142.

[51] Int. Cl.$^3$ ................................................ C07F 9/38

[52] U.S. Cl. .............................................. 260/502.5 F
[58] Field of Search ................................. 260/502.5 F

[56] References Cited

U.S. PATENT DOCUMENTS 3,288,846 11/1966 Irani et al. ..................... 260/502.5 F
4,369,142 1/1983 Moser ........................... 260/502.5 F

*Primary Examiner*—J. E. Evans
*Attorney, Agent, or Firm*—Karl F. Jorda

[57] ABSTRACT

The novel process for producing N-phosphonomethylglycine comprises reacting aminomethanephosphonic acid with glyoxal, in an aqueous medium, in the presence of sulfur dioxide. The active substance obtained is a herbicide having a very wide spectrum of activity.

3 Claims, No Drawings

PROCESS FOR PRODUCING N-PHOSPHONOMETHYLGLYCINE

CROSS REFERENCE TO RELATED APPLICATIONS

This is a divisional of application Ser. No. 442,933 filed on Nov. 19, 1982, now U.S. Pat. No. 4,486,358 which is a continuation-in-part of application Ser. No. 391,816, filed June 24, 1982, now abandoned, which is a continuation-in-part of application Ser. No. 327,138, filed Dec. 3, 1981, now U.S. Pat. No. 4,369,142, issued Jan. 18, 1983.

The present invention relates to a novel process for producing N-phosphonomethylglycine of the formula I

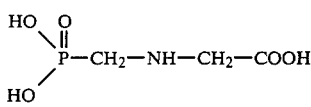 (I)

by reaction of aminomethanephosphonic acid with glyoxal in an aqueous medium in the presence of sulfur dioxide.

N-Phosphonomethylglycine is a herbicide which has a very wide spectrum and which has little or no residual effects. The production and use thereof are described in the U.S. Pat. No. 3,799,758.

It is known that on reaction of glycine, formaldehyde and phosphorous acid in the molar ratio of 1:1:1, there is formed, instead of the desired N-phosphonomethylglycine mainly N,N-bis-phosphonomethylglycine (cp. U.S. Pat. No. 3,956,370). This product can then be converted electrolytically (U.S. Pat. No. 3,835,000) into phosphonomethylglycine.

In order to overcome the difficulties associated with the aforementioned process, it has been suggested that N-phosphonomethylglycine be produced by a process comprising firstly reacting an N-substituted glycine with formaldehyde and phosphorous acid to the corresponding N-substituted N-phosphonomethylglycine, and subsequently detaching from this the substituent originally present on the nitrogen atom. There is thus described for example in the U.S. Pat. No. 3,956,370 the production of N-phosphonomethylglycine by reaction of N-benzylethylglycinate with formaldehyde and phosphorus acid with simultaneous hydrolysis of the ester group to give N-benzyl-N-phosphonomethylglycine and subsequent removal of the benzyl groups, as benzyl bromide, with strong hydrobromic acid. N-Phosphonomethylglycine is obtained in this manner in a yield of about 40%. This process is not advantageous for commercially producing N-phosphonomethylglycine on account of the low yield and in view of the lacrimatoric action of the benzyl bromide formed as a by-product.

It is therefore the object of the present invention to provide a process by which N-phosphonomethylglycine can be produced in good yield and with the formation of by-products which are easy to handle and environmentally favourable.

It is suggested according to the invention to produce N-phosphonomethylglycine by reacting aminomethanephosphonic acid of the formula II

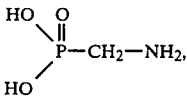 (II)

in an aqueous medium, with glyoxal of the formula III

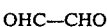 (III)

in the presence of sulfur dioxide, and isolating the resulting product.

There are two preferred procedures in performing the reaction according to the invention.

The first advantageous procedure for the reaction is to suspend the aminomethanephosphonic acid and glyoxal in water, and to subsequently introduce sulfur dioxide into the suspension.

In this procedure the introduction of the sulfur dioxide gas can be performed with or without cooling of the reaction solution. The reaction mixture is however advantageously cooled to 0° to 30° C., particularly to 5° to 20° C., during the time the sulfur dioxide gas is being introduced. The amount of sulfur dioxide gas introduced is so regulated that the amount is between that required to clarify the suspension and that sufficing to saturate the mixture. A saturation of the reaction solution with sulfur dioxide is however an advantage.

The second advantageous procedure for the reaction is to suspend the aminomethanephosphonic acid in water and to subsequently introduce the glyoxal and the sulfur dioxide into the suspension simultaneously.

In this procedure the addition of the glyoxal and the sulfur dioxide gas is with advantage performed in a pre-heated suspension of aminophosphonic acid. The temperature of the suspension is preferably 30° to 90° C., and in particular 35° to 75° C.

The amount of sulfur dioxide employed in this type of procedure may be less than the equivalent necessary to form the bis-adduct with glyoxal. Preferred amounts of sulfur dioxide are 0.3 to 1.5 mole per mole of glyoxal. Most preferred are 0.5 to 1.0 mole sulfur dioxid gas per mole of glyoxal.

After completion of the introduction of the sulfur dioxide, resp. the glyoxal and the sulfur dioxide, required, in both procedures the solution is heated to a temperature of between 60°and 120° C. A temperature of between 85° C. and the boiling temperature of the reaction mixture is advantageous. The reaction solution is heated for a period of 5 to 120 minutes. Reaction times of 15 to 60 minutes, and in particular of 20 to 40 minutes, are advantageous. The sulfur dioxide gas introduced is again liberated during heating and can be recovered.

The employed glyoxal can be used, in the reaction according to the invention, both as an aqueous solution of the monomer and as polymer.

In order to obtain a high yield, it is of advantage to keep the amount of water as small as possible, since the reaction product is soluble in water. The further addition of water as solvent can be dispensed with in particular when dilute aqueous solutions of glyoxal are being used.

In the reaction according to the invention, the sulfur dioxide can also be in the bound form instead of being in the form of sulfur dioxide gas. Especially suitable in this respect are alkali metal salts and alkaline-earth metal salts of sulfurous acid, particularly hydrogen sulfite of sodium, potassium or calcium.

Using the procedure of adding the glyoxal to a suspension of aminomethanephosphonic acid and an alkali metal hydrogen sulfite very small amounts of the hydrogen sulfite may be used. Even amounts of less than 0.05 mole of sodium hydrogen sulfite per mole of glyoxal do not lower the yield dramatically. In this case a heating of the reaction mixture to temperature about 75° C. is not advisable, in order to avoid an evolution of sulfur dioxide gas, which would stop the reaction before having achieved a reasonable conversion of the starting materials. The reaction still works at concentrations of 0.01 mole of alkali metal hydrogen sulfite per mole of glyoxal, but the reaction rates become slower with decreasing concentrations. Reaction times required may be up to 3 hours when low concentrations of alkali metal hydrogen sulfite are employed.

Also adducts of glyoxal and sulfurous acid, and salts thereof, can be used as starting products for the reaction according to the invention. Suitable in a particular manner for this purpose is the commercially obtainable glyoxal-bis-(sodium hydrogen sulfite) hydrate.

The substitution of sulfur dioxide by salts thereof or by reaction products of these with glyoxal is advantageous with respect to carrying out the process of the invention in the laboratory by virtue of the greater ease of operation; however, also in the case of applying the process on a commercial scale, the use of sulfur dioxide gas is of advantage for reasons of cost, in particular because the sulfur dioxide released again during the reaction can be recovered and re-utilised in the reaction of the following reaction batch.

An advantageous embodiment of the process according to the invention comprises saturating at 5° to 20° C. the suspension of aminomethanephosphonic acid and glyoxal in water with sulfur dioxide, heating the formed solution at 85° to 105° C. for 20 to 40 minutes, and isolating the product by crystallisation.

Another advantageous embodiment of the process according to the invention comprises introducing at 30° to 90° C. into a suspension of aminomethanephosphonic acid simultaneously glyoxal and sulfur dioxide, heating the formed solution at 85° to 105° C. for 20 to 40 minutes, and isolating the product by crystallisation.

Another advantageous embodiment of the process according to the invention comprises adding at temperatures not above 75° C. glyoxal to a suspension of aminomethanephosphonic acid and at least 0.01 mole of alkalimetal hydrogen sulfite, heating the mixture at temperatures not above 75° C. for 0.5 to 3 hours and isolating the product by crystallisation.

The reactants, aminomethanephosphonic acid and glyoxal, are as a rule reacted in equimolar amounts.

The Examples which follow serve to further illustrate the present invention.

EXAMPLE 1

Sulfur dioxide gas is introduced at 10° to 15° C., with vigorous stirring and with cooling, into a suspension of 11.1 g (0.1 mol) of aminomethanephosphonic acid and 11.4 ml (0.1 mol) of 40% aqueous glyoxal in 40 ml of water until a clear solution has formed. After further stirring at room temperature for half an hour, the solution is refluxed for half an hour, in the course of which an intense evolution of sulfur dioxide occurs, and the solution turns dark brown. The reaction mixture is afterwards cooled to 5° C.; the formed precipitate is separated, washed with a small amount of ice-water and recrystallised from water. The yield is 8.1 g (48%) of pure N-phosphonomethylglycine; decomposition: 236° C.

EXAMPLE 2

A suspension of 11.1 g (0.1 mol) of aminomethanephosphonic acid and 7.2 g (0.1 mol) of 80% polymeric glyoxal in 40 ml of water is treated with sulfur dioxide and further processed in the manner described in Example 1; yield: 7.7 g (45.5%) of N-phosphonomethylglycine; decomposition: 244° C.

EXAMPLE 3

Sulfur dioxide gas is introduced, without cooling and with vigorous stirring, into a suspension of 11.1 g (0.1 mol) of aminomethanephosphonic acid and 7.2 g (0.1 mol) of 80% polymeric glyoxal in 40 ml of water until saturation is attained, in the course of which the solution turns yellowish-orange and the temperature rises to 42° C. The solution is subsequently stirred and refluxed, during which time the colour of the solution becomes dark brown. The solution is filtered hot and then cooled to 5° C.; the precipitate is afterwards separated, washed with a small amount of ice-cold water and dried. The resulting yield is 10.6 g (62.8%) of N-phosphonomethylglycine; decomposition: 235° C.

EXAMPLE 4

A suspension of 15.6 g (0.055 mol) of glyoxal-bis-(sodium hydrogen sulfite) hydrate and 5.5 g (0.05 mol) of aminomethanephosphonic acid in 30 ml of water is refluxed with stirring. The evolution of sulfur dioxide commences when the temperature reaches 87° C.; a clear solution is formed and is refluxed for 40 minutes. After cooling of the reaction mixture to room temperature, 11 ml (0.11 mol) of 32% hydrochloric acid are added, and the mixture is concentrated by evaporation. The oily residue is triturated with 40 ml of 36% hydrochloric acid; the salt which has precipitated is then separated, and the solution is again concentrated by evaporation. The oil obtained is crystallised by the addition of 150 ml of ethanol. This suspension is neutralised to Congo red by propylene oxide being added; the precipitate is separated, washed with ethanol and dried. Recrystallisation from water yields 4.5 g (53.2%) of N-phosphonomethylglycine; decomposition: 228° C.

EXAMPLE 5

A suspension of 22.2 g (0.2 mol) of aminomethanephosphonic acid and 58 g (0.2 mol) of glyoxal-bis-(sodiumhydrogen sulfite) hydrate in 80 ml aqueous 5 N hydrochlorid acid is heated slowly, while stirring, until the temperature reaches 95° C. When the temperature at the interior of the reaction vessel reaches 70° C., a strong evolution of sulfur dioxide occurs and the colour of the solution becomes light brown. After the gas-evolution has ceased, the reaction mixture is boiled for 0.5 hour under reflux, and then slowly cooled down to 0° C. The precipitation that falls out, is filtered off, washed with icecold water and with acetone and then dried. Thus 20.2 g (59.8%) of N-phosphonomethylglycine is obtained, which melts while decomposing at 236° C.

EXAMPLE 6

26 g (0.4 mol) Sulfur dioxide gas and 58 g of a 40% aqueous solution of glyoxal (0.4 mol) are simultaneously introduced at a temperature of 40° C. into a suspension of 44.4 g (0.4 mol) of aminomethanephosphonic acid in 160 ml of water. The resulting solution is refluxed for 30 minutes, in course of which an evolution of sulfur dioxide occurs. The solution is then cooled to 5° C.; the formed precipitate is separated, washed with a small amount of ice-water and dried. The resulting yield is 44 g (65%) of N-phosphonomethylglycine; decomposition: >250° C.

EXAMPLE 7

26 g (0.4 mol) Sulfur dioxde gas and 58 g of a 40% aqueous solution of glyoxal (0.4 mol) are simultaneously introduced at a temperature of 60° C. into a suspension of 44.4 g (0.4 mol) of aminomethanephosphonic acid in 160 ml of water. The resulting solution is refluxed for 30 minutes, in course of which an evolution of sulfur dioxide occurs. The solution is then cooled to 5° C.; the formed precipitate is separated, washed with a small amount of ice-water and dried. The resulting yield is 50 g (74%) of N-phosphonomethylglycine; decomposition: >250° C.

EXAMPLE 8

13 g (0.2 mol) Sulfur dioxide gas and 58 g of a 40% aqueous solution of glyoxal (0.4 mol) are simultaneously introduced at a temperature of 60° C. into a suspension of 44.4 g (0.4 mol) of aminomethanephosphonic acid in 160 ml of water. The resulting solution is refluxed for 30 minutes, in course of which an evolution of sulfur dioxide occurs. The solution is then cooled to 5° C.; the formed precipitate is separated, washed with a small amount of ice-water and dried. The resulting yield is 50 g (74%) of N-phosphonomethylglycine; decomposition: >250° C.

EXAMPLE 9

50.5 g of a 40% aqueous solution of glyoxal (0.334 mol) is dropwise added to a solution of 37.1 g (0.334 mol) of aminomethanephosphonic acid and 2.6 g (0.016 mol) of sodium hydrogen sulfite in 150 ml of water at a temperature of 60° C. Stirring of the mixture at the same temperature is continued for 1 hour; the mixture is cooled to 5° C.; the formed precipitate is separated, washed with a small amount of ice-water and dried. The resulting yield is 37.6 g (67%) of N-phosphonomethylglycine; decomposition: >250° C.

What is claimed is:

1. A process for producing N-phosphonomethylglycine of the formula I

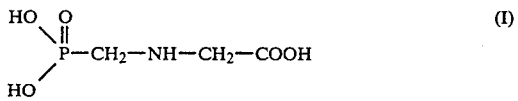

by reacting aminomethanephosphonic acid of the formula II

with glyoxal of the formula III

in an aqueous medium and in the presence of sulfur dioxide, said glyoxal being added to a suspension of said aminomethanephosphonic acid and an alkali metal hydrogen sulfite as a source of sulfur dioxide, and isolating the resulting product.

2. A process according to claim 1, wherein the amount of alkali metal hydrogen sulfite is at least 0.01 mole per mole of glyoxal.

3. A process according to claim 1, wherein glyoxal is added at a temperature not above 75° C. to a suspension of aminomethanephosphonic acid and at least 0.01 mol of alkali metal hydrogen sulfite, the mixture is heated at a temperature not above 75° C. for 0.5 to 3 hours, and the product is isolated by crystallization.

* * * * *